(12) United States Patent
Pines et al.

(10) Patent No.: US 6,652,833 B2
(45) Date of Patent: Nov. 25, 2003

(54) FUNCTIONALIZED ACTIVE-NUCLEUS COMPLEX SENSOR

(75) Inventors: Alexander Pines, Berkeley, CA (US); David E. Wemmer, Berkeley, CA (US); Megan Spence, Oakland, CA (US); Seth Rubin, Albany, CA (US)

(73) Assignee: The Regents of the University of California, Oakland, CA (US)

(*) Notice: Subject to any disclaimer, the term of this patent is extended or adjusted under 35 U.S.C. 154(b) by 3 days.

(21) Appl. No.: 09/903,279

(22) Filed: Jul. 11, 2001

(65) Prior Publication Data

US 2002/0037253 A1 Mar. 28, 2002

Related U.S. Application Data

(60) Provisional application No. 60/218,549, filed on Jul. 13, 2000.

(51) Int. Cl.[7] .......................... A61B 5/055; G01N 24/00
(52) U.S. Cl. ........................ 424/9.3; 424/9.37; 436/173
(58) Field of Search ............................... 424/9.3, 9.37, 424/1.65, 9.4; 436/173

(56) References Cited

U.S. PATENT DOCUMENTS

| | | |
|---|---|---|
| 5,357,959 A | 10/1994 | Fishman |
| 5,642,625 A | 7/1997 | Cates, Jr. et al. |
| 5,665,777 A | 9/1997 | Fesik et al. |
| 5,688,486 A * | 11/1997 | Watson et al. .............. 424/1.65 |
| 5,698,401 A | 12/1997 | Fesik et al. |
| 5,785,953 A | 7/1998 | Albert et al. |
| 5,804,390 A | 9/1998 | Fesik et al. |
| 5,846,517 A | 12/1998 | Unger |
| 5,891,643 A | 4/1999 | Fesik et al. |
| 5,989,827 A | 11/1999 | Fesik et al. |
| 6,023,162 A | 2/2000 | Johnson |
| 6,042,809 A | 3/2000 | Tournier et al. |
| 6,051,208 A | 4/2000 | Johnson et al. |
| 6,071,494 A * | 6/2000 | Unger ......................... 424/9.4 |
| 6,288,261 B1 | 9/2001 | Augeri et al. |
| 6,426,058 B1 | 7/2002 | Pines et al. |
| 2002/0131900 A1 * | 9/2002 | Jensen ...................... 422/82.05 |

FOREIGN PATENT DOCUMENTS

EP  0 620 447 A2  4/1994

OTHER PUBLICATIONS

Faruqu, Tatjana R. et al.; "Structure–Function Analysis of Protease–Activated Receptor 4 Tethered Ligand Peptides," Journal of Biological Chemistry, vol. 275, No. 26, pp. 19728–19734, Jun. 30, 2000.

Bartik, Kristin et al.; "129 XE and 1H NRM Study of the Reversible Trapping of Xenon by Cryptophane–A in Organic Solution," Journal of American Society, vol. 120, pp. 784–791, (1998).

Solomon, L., "Relaxation Processes in a System of Two Spins," Physical Review, vol. 99, No. 2, pp. 559–565, Jul. 15, 1955.

Mansfield, P., "Multi–Planar Image Formation Using NMR Spin Echoes," Journal of Physical Chemistry: Solid State Physics, vol. 10, pp. L55 thru L58, (1977).

Haase, A., Frahm, J., Matthael, D., Hanicke, W., and Merboldt, K.D., "Flash Imaging. Rapid NMR Imaging Using Low Flip–Angle Pulses," Journal of Magnetic Resonance, vol. 67, pp. 258–266, (1986).

Raftery, D., Long, H., Meersmann, T., Grandinetti, P.J., Reven, L., and Pines, A., "High–Field NMR of Absorbed Xenon Polarized by Laser Pumping," Physical Review Letters, vol. 66, No. 5, pp. 584–587, Feb. 4, 1991.

Long, H.W., Gaede, H.C., Shore, J., Reven, L., Bowers, C.R., Kritzenberge, J., Pietrass, T., and Pines, A., High–Field Cross Polarization NMR From Laser–Polarized Xenon to a Polymer Surface, Journal of the American Chemical Society, vol. 115, No. 18, pp. 8491–8492, Nov. 18, 1993.

Bartik, Kristin et al.; "129 Xe and 1H NMR Study of the Reversible Trapping of Xenon by Cryptophane–A in Organic Solution," J. Am. Chem. Soc., vol. 120, pp. 784–791, (1998).

Faruqi, Tatjana R. et al., "Structure–Function Analysis of Protease–Activated Receptor 4 Tethered Ligand Peptides," Journal of Biological Chemistry, Vo. 275, No. 26, pp. 19728–19734, Jun. 30, 2000.

Hall, Jason A. et al.; "Two Modes of Ligand Binding in Multose–Binding Protein of *Escherichia coli*," vol. 272, No. 28, pp. 17605–17609, Jul. 11, 1997.

\* cited by examiner

*Primary Examiner*—Michael G. Hartley
(74) *Attorney, Agent, or Firm*—O'Banion & Ritchey; James M. Ritchey

(57) ABSTRACT

A functionalized active-nucleus complex sensor that selectively associates with one or more target species, and a method for assaying and screening for one or a plurality of target species utilizing one or a plurality of functionalized active-nucleus complexes with at least two of the functionalized active-nucleus complexes having an attraction affinity to different corresponding target species. The functionalized active-nucleus complex has an active-nucleus and a targeting carrier. The method involves functionalizing an active-nucleus, for each functionalized active-nucleus complex, by incorporating the active-nucleus into a macromolucular or molecular complex that is capable of binding one of the target species and then bringing the macromolecular or molecular complexes into contact with the target species and detecting the occurrence of or change in a nuclear magnetic resonance signal from each of the active-nuclei in each of the functionalized active-nucleus complexes.

9 Claims, 13 Drawing Sheets

FUNCTIONALIZED ACTIVE-NUCLEUS COMPLEX SENSOR

Priority is claimed to Provisional Application No. 60/218,549 that was filed on Jul. 13, 2000.

This research was supported by the Director, Office of Energy Research, Office of Basic Energy Sciences, Materials Sciences Division, Physical Biosciences Division, of the U.S. Department of Energy under Contract No. DE-AC03-76SF00098. Additionally, support was provided by the National Science Foundation Pre-Doctoral Fellowship Program.

BACKGROUND OF THE INVENTION

1. Field of the Invention

A molecular or macromolecular structure and method of use are disclosed in which an active-nucleus is functionalized in at least a transient interaction with a target carrier to form a sensor that selectively associates with a target substrate or environment to produce a detectable signal. More specifically, a functionalized active-nucleus complex sensor is described in which an active-nucleus gas such as hyperpolarized xenon, hyperpolarized helium, or sulfur hexafluoride, or active-nuclei $^{19}$F derivatives are bound in a carrier structure having a binding region specific for a target species. Upon binding to the target species the active-nucleus produces a detectable nuclear magnetic resonance signal or is detectable as a magnetic resonance imaging contrast agent. A plurality of target specific sensors may be utilized in the assaying and screening of samples containing the plurality of targets under either in vivo or in vitro conditions.

2. Description of the Background Art

The detection of biological molecules and their interactions is a significant component of modern biomedical research. In current biosensor technologies, simultaneous detection is limited to a small number of analytes by the spectral overlap of their signals. Recent biosensor technologies exploit surface plasmon resonance (1), fluorescence polarization (2), and fluorescence resonance energy transfer as detection methods (3). Although the sensitivity of such techniques is excellent, it has proven challenging to extend these assays to multiplexing capabilities because of the difficulty in distinguishing signals from different binding events. While nuclear magnetic resonance (NMR) spectroscopy is able to finely resolve signals from different molecules and environments, the spectral complexity and low sensitivity of NMR spectroscopy normally preclude its use as a detector of molecular targets in complex mixtures. Notable successes (4,5) in the application of NMR to such problems are still limited by long acquisition times or a limited number of detectable analytes. Laser polarized xenon NMR benefits from good signal to noise and spectral simplicity with the added advantage of substantial chemical shift sensitivity.

U.S. Pat. No. 5,642,625 discloses a high volume hyperpolarizer for spin-polarized noble gas. A method and apparatus are presented that allow spin exchange between atoms of the noble gas and an alkali metal such as rubidium.

Described in U.S. Pat. No. 5,785,953 is a magnetic resonance imaging technique using hyperpolarized noble gases as contrast agents. In particular, hyperpolarized xenon and helium are utilized in spatial distribution studies.

The foregoing references/patents reflect the state of the art of which the applicant is aware and are tendered with the view toward discharging applicant's acknowledged duty of candor in disclosing information which may be pertinent in the examination of this application. It is respectfully submitted, however, that none of these references/patents teach or render obvious, singly or when considered in combination, applicant's claimed invention.

SUMMARY OF THE INVENTION

An object of the present invention is to disclose a sensor and method of use comprising an active-nucleus (guest) and target carrier (host) that generates an NMR and/or MRI detectable signal upon association with a biological target.

Another object of the present invention is to relate a biosensor and method of in vivo and in vitro assaying/screening use that comprises a functionalize active-nucleus complex that selectively binds to and signals the presence of a desired biological target species.

A further object of the present invention is to describe biosensors and methods of in vivo and in vitro assaying/screening use that comprises a plurality of functionalize active-nucleus complexes with each complex selectively binding to and signaling the presence of a desired biological target species or analyte.

Still another object of the present invention is to present a biosensor and method of use in which the biosensor comprises an active-nucleus bound to a target carrier in which when the target carrier binds to a target species/analyte a detectable signal is produced upon the binding or upon alterations in the target species/analyte or its environment after the binding.

Yet a further object of the present invention is to disclose a plurality of biosensors and a multiplexed method of use in which each of the biosensors comprises an active-nucleus bound to a target carrier in which when the target carrier binds to a target species/analyte a detectable signal is produced upon the binding or upon alterations in the target species/analyte or its environment after the binding, wherein all the biosensors' signals are simultaneously detectable.

Disclosed is a novel, functionalized active-nucleus sensor or biosensor that is directed to and signals the presence of a desired biological target species, often of biological origin or importance. An active-nucleus that presents a detectable signal to either nuclear magnetic resonance (NMR) or magnetic resonance imaging (MRI) techniques is utilized in conjunction with a target specific carrier that interacts with both the active-nucleus and a biological target substrate or environment. The active-nucleus is capable of at least a minimal transient binding to a targeting carrier. The targeting carrier associates with the target substrate or environment, thereby stimulating the production of or change in the detectable signal from the active-nucleus in a functionalized interaction. "Functionalized" implies that when the active-nucleus is bound, in at least a minimal transient manner, by the targeting carrier, that the active-nucleus then responds to and signals the association between the targeting carrier and the target substrate or environment.

Since the basic subject invention enables the creation of several extremely powerful and versatile sensors and techniques that have eluded researchers for many years, a number of related embodiments are disclosed below. One requirement for the subject invention is that the reporter nucleus be sufficiently "active" or capable of producing a signal that is detectable by NMR or MRI techniques. Hyperpolarized noble gases such as xenon and helium meet this requirement, as do other nuclei such as $^{19}$F, if present in sufficiently high concentrations. Thus, "active" implies that the nucleus generates a suitable signal that is capable of detection by NMR (either in strong or weak magnetic fields) and/or MRI contrast procedures. Several relatively standard techniques now exist for hyperpolarizing noble gases and include optical pumping or spin exchange procedures.

It is important to appreciate that for the subject invention the signal produced by the functionalized active-nucleus is studied directly to follow the behavior of the biological target substrate or environment. For example, xenon (as indicated above, other suitable active-nuclei are also contemplated as being within the realm of this disclosure), has a chemical shift that is enormously sensitive to its local chemical environment. With the large xenon NMR signal created by optical pumping, the chemical shift can easily serve as a signature for the different chemical surroundings in which the xenon is found. Direct interaction between xenon and a target molecule has been observed by measuring the chemical shift and relaxation properties on xenon (in particular see, S. M. Rubin, M. M. Spence, B. M. Goodson, D. E. Wemmer, A. Pines, *Proceedings of the National Academy of Sciences of the United States of America* 97, 9472–9475 (2000) that was part of the Provisional Application to which this application claims priority). However, the observation is of this direct contact may be limited by the weak binding of xenon (or other suitable active-nuclei) to many target molecules of interest. To enhance the binding of the xenon, for example, to the biological target species/substrate/molecule/analyte of interest, and thus the population of xenon in contact with the target species/substrate/molecule/analyte, the xenon can be functionalized to strongly bind to the biological target species/substrate/molecule/analyte. This can be achieved by placing the xenon, or other suitable active-nuclei, in a target carrier that chemically recognizes and binds to the target. The target carrier has a first binding region that binds the xenon for at least a minimal transient period ("minimal" in the sense of a sufficiently long period of time to produce a useful signal) or, preferably, very strongly binds the xenon, and can not itself quickly relax the xenon polarization. Amplification of the sensing for both xenon and helium may be achieved by utilizing a "pool" of hyperpolarized active-nuclei atoms that either sense the environment by changes in the functionalized active-nucleus carrier complex (molecule, supramolecular, or microbubble environment) or else are in sufficiently rapid chemical exchange with active-nuclei in biosensor sites that are so sensitive, thereby amplifying the detection intensity yet further.

The target carrier has a second binding region that binds to or reacts with the target species/substrate/molecule/analyte. The target carrier allows xenon, or other active-nuclei, to be held in close proximity to the desired target, giving rise to a signal at a distinctive frequency indicating the presence of the target species/substrate/molecule/analyte. The functionalized active-nucleus/target carrier complex can "recognize" any one of a wide variety of biological target species/substrates/molecules/analytes (virtually an unlimited set of organic/biomolecular structures) including biologically important species such as proteins, nucleic acids, carbohydrates, lipids, metabolites, and the like in either an in vitro or non-invasive in vivo setting at either high or low NMR utilized field strengths. For example, with diseases, the diagnostic power of the subject invention is quite clear. Various diseases present characteristic/defining targets such as unusual membrane proteins, lipids, or carbohydrates, unusual analytes in body fluids, and the like whose presence can easily be detected with the subject invention.

The subject method of assaying and screening for target species in in vivo and in vitro samples/subjects has many strengths, including the large signal to noise ratio afforded by the high polarization achieve with hyperpolarization of xenon, helium, and other suitable nuclei. With xenon, for example, there is a negligible natural presence of xenon, so there would be no interference from background xenon signals. In contrast to fluorescence (and other techniques that generate overlapping or interfering detection signals) assays and screening procedures, multiple functionalized active-nuclei tests are possible in one system (test-tube, plate, microplate, and the like), by creating active-nuclei carriers targeting different species/substrates/molecules/analytes or by altering the structure of the probe itself or both (see below). Each target would give rise to a separate active-nucleus chemical shift. These assays and screenings could also be carried out non-invasively in vivo, avoiding the exposure to radiation that radiometric assays and screenings require. In the case of optical pumping to create hyperpolarization of xenon and helium, because the large active-nuclei signals are generated by the optical pumping, high magnetic fields are unnecessary (as mentioned previously), and the chemical shifts can be detected in low magnetic fields using a superconducting quantum interference device (SQUID).

A preliminary calculation was performed (verified by the results obtained in Experimental Example #1, found below) to explore the initial feasibility of the subject technique in vivo. Based on capabilities of current spectroscopy, 200 nanomoles of nuclear spins are necessary to measure a signal. To compete with or match other forms of assays or screening procedures, 20 picomoles of target species must be detectable, A factor of $10^4$ in signal is required. The hyperpolarization compensates for at least a factor of $10^3$, and the additional factor of ten is gained by the relatively simplicity of the spectrum, contrasted with a target (protein and the like) spectrum.

In its most basic configuration the subject invention comprises an active-nucleus and a target carrier that associates with both the active-nucleus and a desired target species to produce an detectable characteristic signal (typically a chemical shift or relaxation time for NMR or a contrast capability for MRI). The functionalized active-nucleus complex or subject biosensor that may comprise one or more identical or varied second binding regions. Additionally, the functionalized active-nucleus complex or subject biosensor may have varied first binding regions. Also, both the first and second binding regions could be varied within the same subject biosensor. As indicated, the subject invention allows a huge array of possible target species/substrates/molecules/analytes to be assayed/screened for in a parallel or multiplexing detection style within a single sample/subject.

Several possible active-nuclei gases exist, preferable hyperpolarized xenon and hyperpolarized helium, however, $^{19}F$ and similar nuclei, in sufficient concentration, are also contemplated. With fluorine atoms, an exemplary functionalized sensor comprises a target carrier having multiple fluorines such as a polyfluorinated dendrimer that selectively binds an organic target species/substrate/molecule/analyte or a form of fluorine such as sulfur hexafluoride trapped/bound within a functionalized (target specific binding) enclosing structure such as in "bubble" or "microbubble" environment as exemplified by a liposome, micelle, vesicle, bucky-ball type structures, natural and synthetic polymeric cages, and like. Conformational changes or alterations in the effective pressure on the "bubble" or "microbubble" would induce detectable signal variations from the subject biosensor. Variations in the immediate vicinity or environment of the biosensor should be detectable and include changes in ion concentrations, functioning of an ion channel, oxygen levels/distribution, neuron activity, and the like. It is noted that hyperpolarized xenon and hyperpolarized helium will also function as the signal reporting active-nuclei within similar functionalized "bubble" or "microbubble" structures.

The first binding region of the targeting carrier interacts/associates/binds with the active-nucleus. This first binding region includes structures such as monoclonal antibodies, dendrimers, self-assembled lipid complexes, liposomes, cyclodextrins, cryptands, carcerands, microbubbles, micelles, vesicles, molecular tennis balls, fullerenes, many general cage-like structures, and the like.

The second binding region in the targeting carrier comprises that portion of the subject biosensor that interacts with the target species/substrate/molecule/analyte. It is noted that multiple second binding regions are contemplated and may be identical or varied for attachment to a plurality of target sites.

The basic subject biosensor may contain additional useful components/structures. One or more "tether" regions may be included and serve to separate the first and second binding regions and to permit a region that may be further derivatized with additional moieties such as solubilizing regions. The solubilizing regions may contain polypeptides, carbohydrates, and other species that aid in solubilizing the subject probe.

More specifically, a functionalized active-nucleus biosensor is disclosed that capitalizes on the enhanced signal to noise, spectral simplicity, and chemical shift sensitivity of suitable active-nuclei gases (for example only and not by way of limitation, hyperpolarized xenon, hyperpolarized helium, and sulfur hexafluoride) and polyfluorinated containing species (utilized to target organic molecules) to detect specific targets. One subject sensor embodiment utilizes laser polarized xenon "functionalized" by a biotin-modified supramolecular cage, including a tether region having a solubilizing region, to detect biotin-avidin binding. This biosensor methodology can be used in analyte assays and screening procedures or extended to multiplexing assays for multiple analytes of screenings for multiple species.

Other objects, advantages, and novel features of the present invention will become apparent from the detailed description that follows, when considered in conjunction with the associated drawings.

DESCRIPTION OF THE PREFERRED EMBODIMENT

Figure 1:
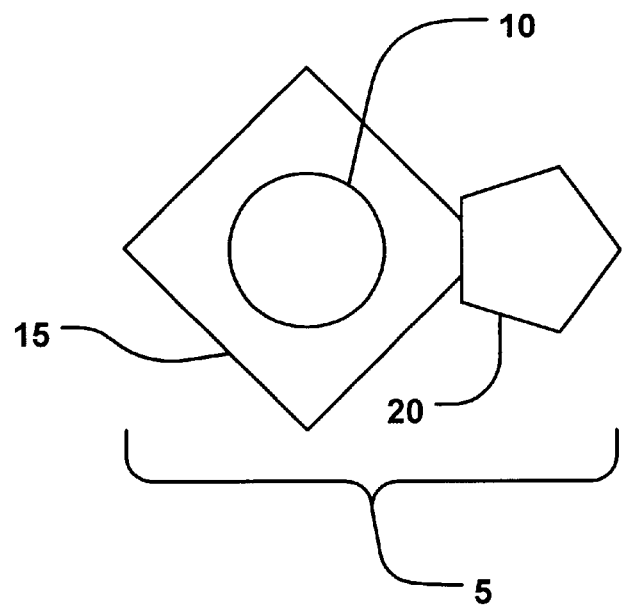
FIG. 1 is a schematic model showing a first embodiment of the subject sensor illustrating a first binding region for holding the active-nucleus and a second binding region that associates with the target.
Figure 2:
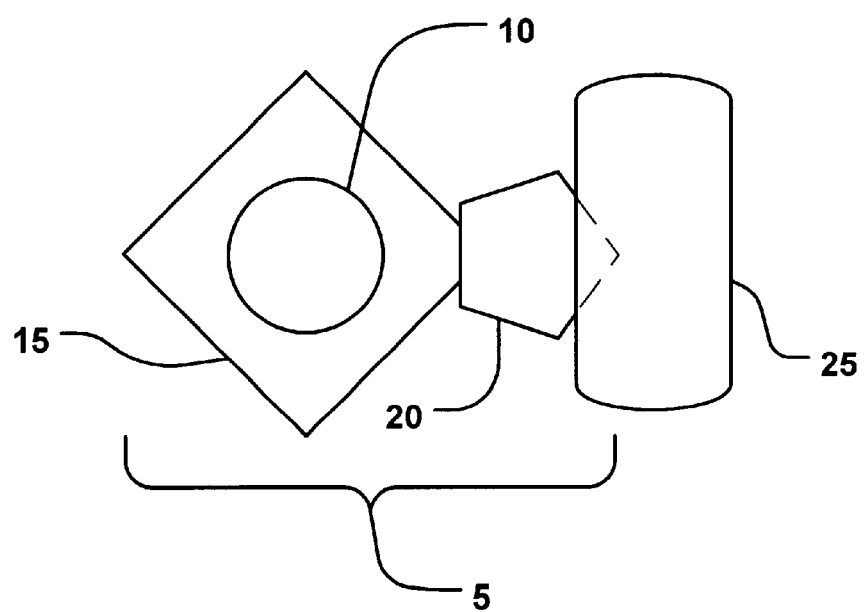
FIG. 2 is the schematic model sensor shown in FIG. 1 with a target species bound to the second binding region.

There are several preferred embodiments of the subject invention disclosed in the specification and depicted in FIGS. 1–15. In the subject invention's most basic configuration the subject invention comprises an active-nucleus (NMR or MRI detectable nuclei, preferably hyperpolarized xenon or hyperpolarized helium, however, $^{19}$F is useful if present at sufficient levels) and a target carrier that associates with both the active-nucleus and a desired target to produce an detectable characteristic signal (typically a chemical shift or relaxation time for NMR or a contrast capability for MRI). FIG. 1 depicts the basic biosensor (the functionalized active-nucleus complex) 5 configuration and FIG. 2 shows the basic functionalized biosensor 5 bound to a target species/substrate/molecule/analyte 25. An active-nucleus 10 is bound in a targeting carrier. The targeting carrier comprises, at least, a first binding region 15, binding the active-nucleus, and a second binding region 20, wherein the second binding region 20 has a binding affinity for the target species/substrate/molecule/analyte 25 (the dashed line indicating the binding domain in the target). The detectable signal generated from the bound complex 5 in FIG. 2 is distinguishable from the detectable signal produced from the unbound complex 5 in FIG. 1 (see FIG. 13 for an equivalent signal shift).

Figure 3:
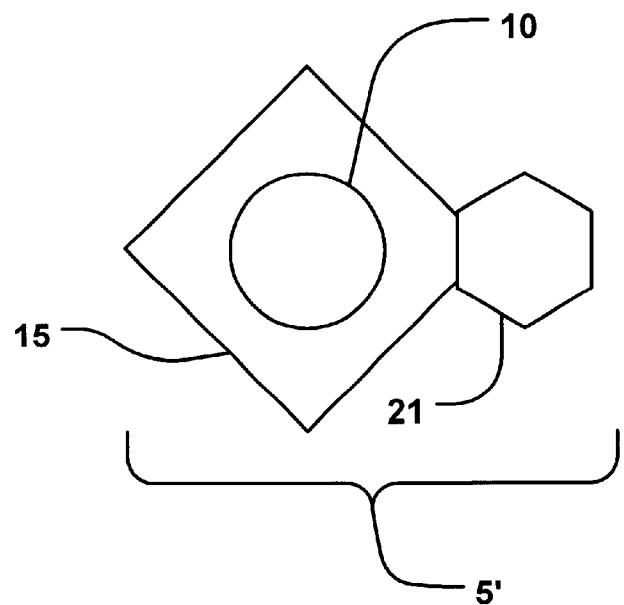
FIG. 3 is a schematic model showing a second embodiment of the subject sensor illustrating a first binding region identical to that depicted in FIG. 1 and a varied second binding region.

As indicated above, one extremely useful characteristic of the subject invention is that the signal produced from the subject sensor is highly dependent upon its immediate environment and that signals created from similar, but not identical, sensors can be distinguished and utilized to detect multiple target species/substrates/molecules/analytes within the same sample. For example, FIG. 3 depicts a functionalized active-nucleus complex or subject biosensor 5' that has a varied second binding region 21, relative to the second binding region 20 seen in FIGS. 1 and 2. Thus, biosensor 5' would bind to a different target species/substrate/molecule/analyte or a different location on the original target species/substrate/molecule/analyte 25.

Figure 4:
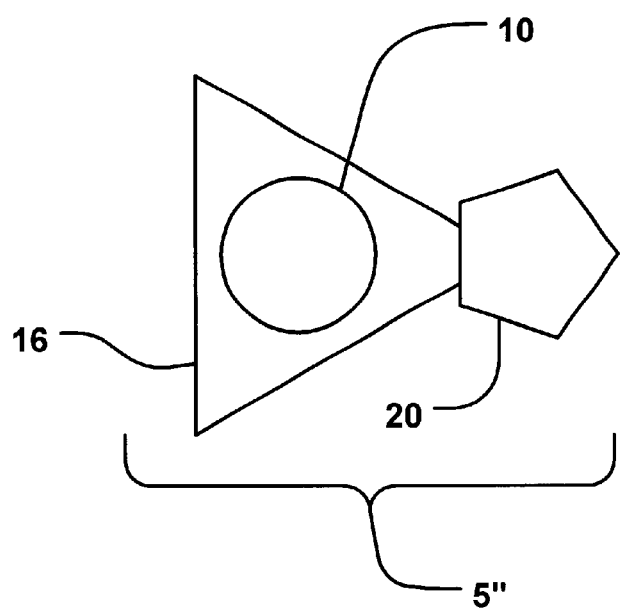
FIG. 4 is a schematic model showing a third embodiment of the subject sensor illustrating a varied first binding region and a second binding region identical to that depicted in FIG. 1.

Additionally, FIG. 4 illustrates a functionalized active-nucleus complex or subject biosensor 5" that has a varied first binding region 16, relative to the first binding region 15 seen in FIGS. 1 and 2. Thus, biosensor 5" would generate a different signal than the signal produced by biosensor 5.

Figure 5:
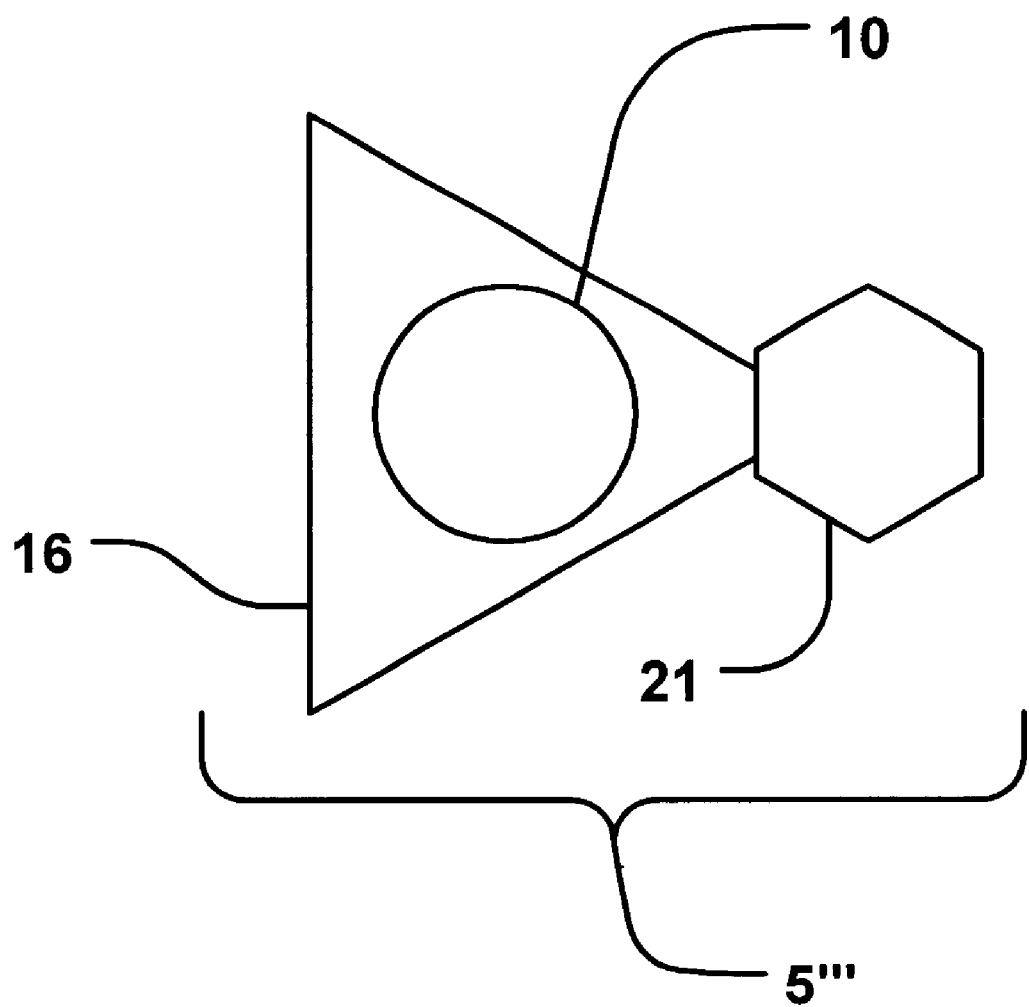
FIG. 5 is a schematic model showing a fourth embodiment of the subject sensor illustrating both a varied first binding region and a varied second binding region, relative to those seen in FIG. 1.

Also, both the first 16 and second binding regions 21 could be varied, relative to the biosensor seen in FIGS. 1 and 2, within the same subject biosensor to form biosensor 5''', as seen in FIG. 5. As indicated, the subject invention allows a huge array of possible target species/substrates/molecules/analytes to be assayed/screened for in a parallel or multiplexing detection style within a single sample.

Figure 6:
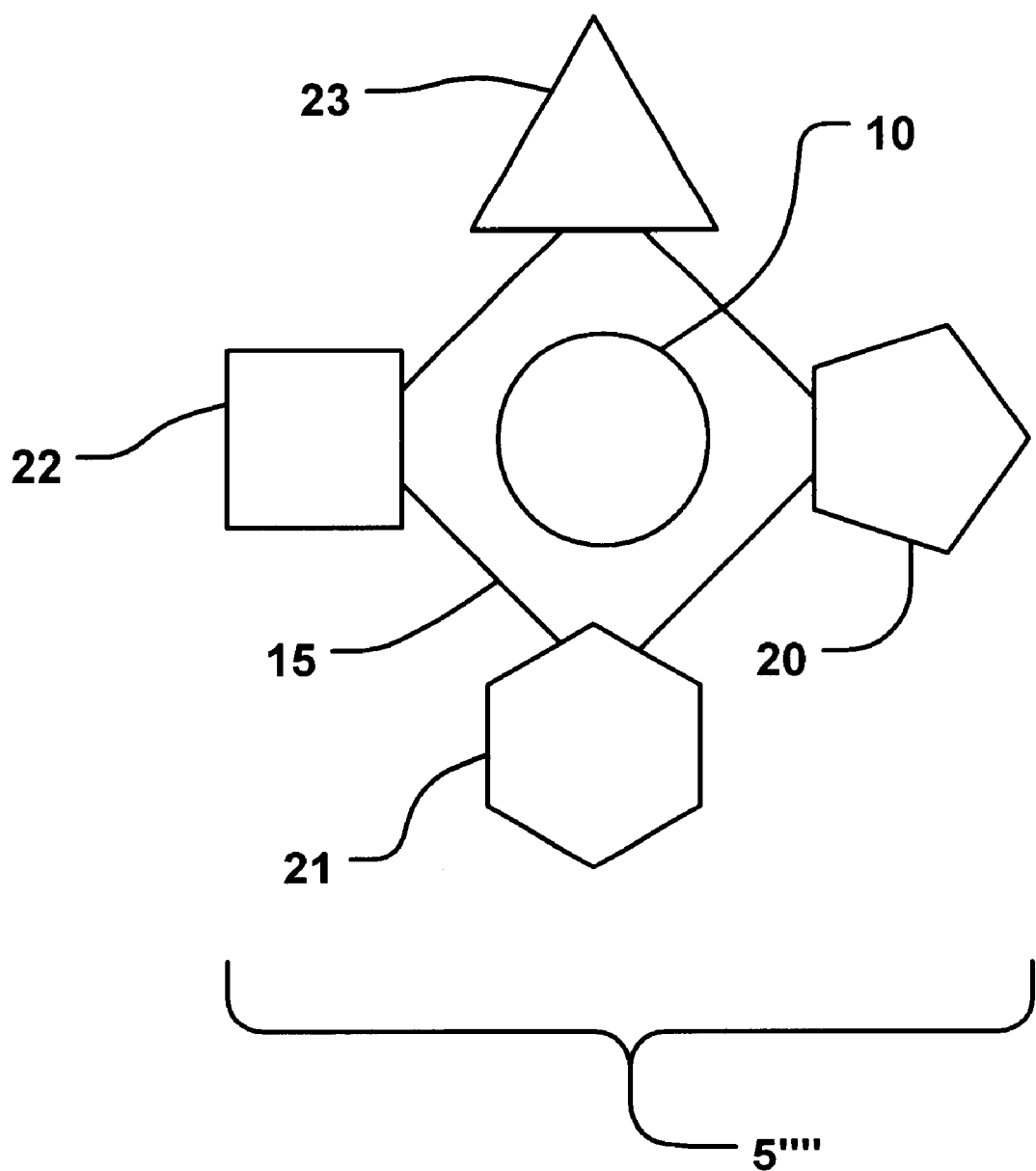
FIG. 6 is a schematic model showing a fifth embodiment of the subject sensor illustrating a first binding region and a plurality of varied second binding regions.

FIG. 6 illustrates a subject biosensor that has several different second binding regions 20, 21, 22, and 23 attached to a first binding region producing sensor 5"". Sensor 5"" may bind to one or more targets via the presented second binding regions.

Figure 7:
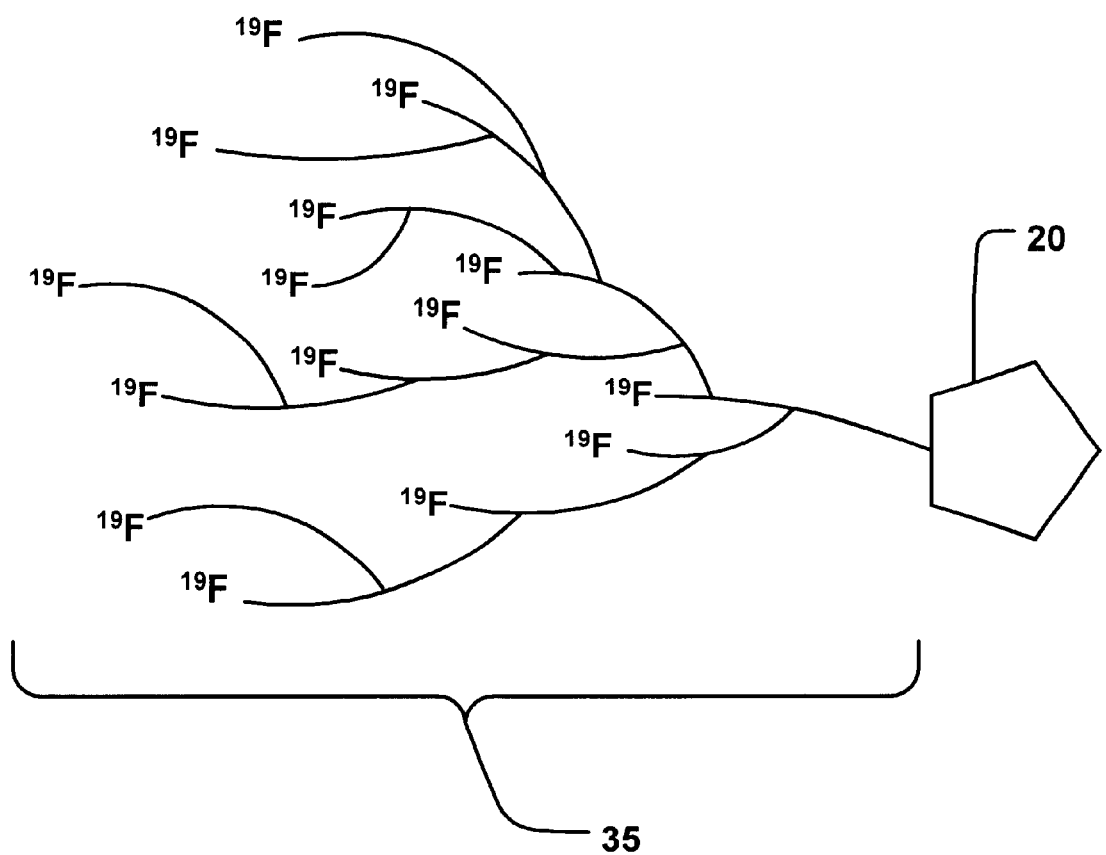
FIG. 7 is a schematic model showing a sixth embodiment of the subject sensor illustrating a polyfluorinated first binding region and a second binding region that associates with an organic target species.
Figure 8:
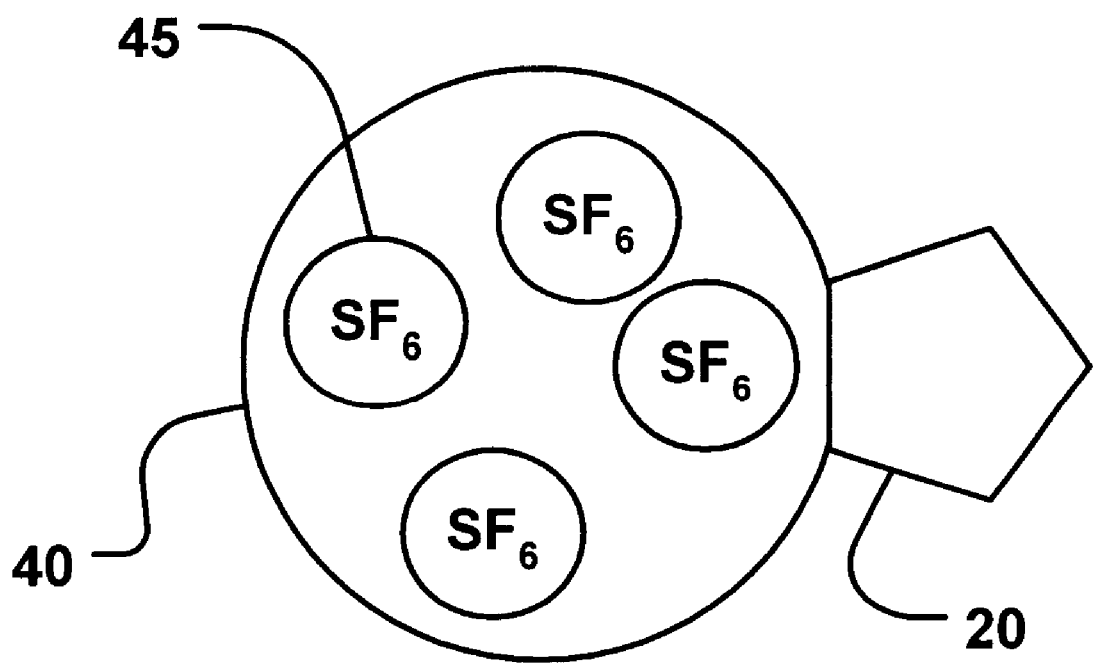
FIG. 8 is a schematic model showing a seventh embodiment of the subject sensor illustrating a first binding region containing sulfur hexafluoride and a second binding region.

As indicated, several possible active-nuclei gases exist for any target species, preferable hyperpolarized xenon, hyperpolarized helium, and sulfur hexafluoride, however, $^{19}$F, in sufficient concentration, is also contemplated for organic/biological targets. With fluorine atoms, an exemplary functionalized sensor comprises a target carrier having multiple fluorines such as a polyfluorinated dendrimer that selectively binds an organic/biological target species/substrate/molecule/analyte, as seen in FIG. 7. The polyfluorinated first binding region 35 may be a dendrimer or other suitable structure, including, but not limited to natural and synthetic polymers and the like. Additionally, sufficient fluorine to produce an acceptable signal may be in the form of fluorine in sulfur hexafluoride and similar compounds. FIG. 8 illustrates sulfur hexafluoride 45 trapped/bound within a functionalized (target specific binding) enclosing structure 40 such as in "bubble" or "microbubble" environment as exemplified by a liposome, micelle, vesicle, bucky-ball type structures, natural and synthetic polymeric cages, and the like. A second binding region 20 is coupled to the enclosing structure 40 and binds the target. Conformational changes or alterations in the effective pressure on the "bubble" or "microbubble" would induce detectable signal variations from the active-nucleus in a subject biosensor. Variations in the immediate vicinity of the biosensor should be detectable and include such changes as: ion concentrations, oxygen levels, neuron activity, and the like. It is noted that hyperpolarized xenon and hyperpolarized helium will also function as signal reporting active-nuclei within similar functionalized "bubble" or "microbubble" structures.

It is noted that the subject targeting carrier comprises the first binding region (15 and 16 in FIGS. 1–6) that interacts/associates/binds with the active-nucleus. This first binding region includes structures such as monoclonal antibodies, dendrimers, self-assembled lipid complexes, liposomes, cyclodextrins, cryptands, cryptophanes, carcerands, microbubbles, micelles, vesicles, molecular tennis balls, fullerenes, many general cage-like structures, and the like. As long as structure or chemical nature of the first binding region permits effective signal producing interactions with the active-nucleus and binding to the target is not negated, a wide range of acceptable structures exists for this portion of the subject biosensor (the chemical shifts or relaxation times for the active-nucleus need to maintained as detectable).

Further, it is stressed that the second binding region (20, 21, 22, and 23 in FIGS. 1–6) in the targeting carrier comprises that portion of the subject biosensor that interacts with the target species/substrate/molecule/analyte. The first and second binding regions may be essentially identical, overlapping, or coextensive or separated by a plurality of atoms.

Figure 9A:
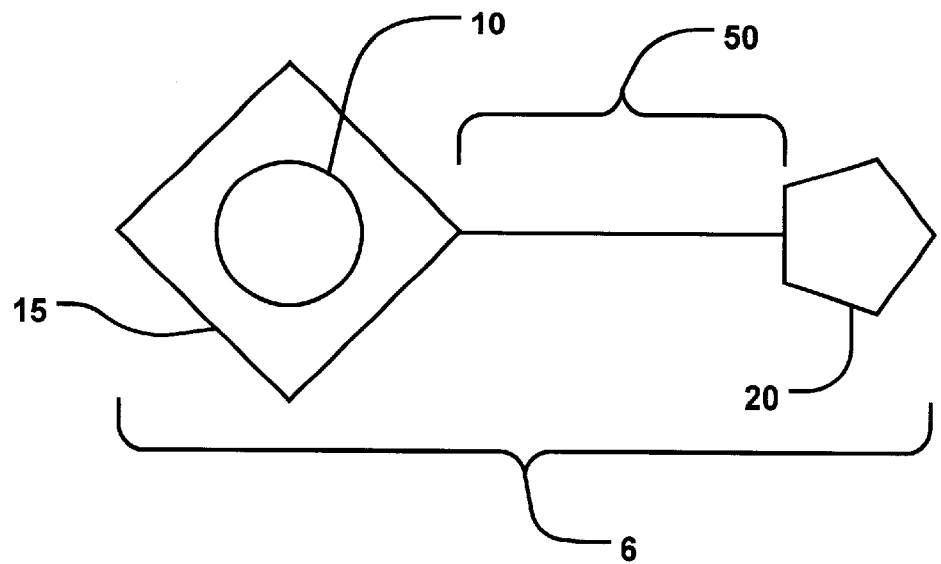
FIG. 9A is a schematic model showing an eighth embodiment of the subject sensor illustrating a first binding region for holding the active-nucleus, a second binding region that associates with the target, and a tether region that connects the first and second binding regions.
Figure 9B:
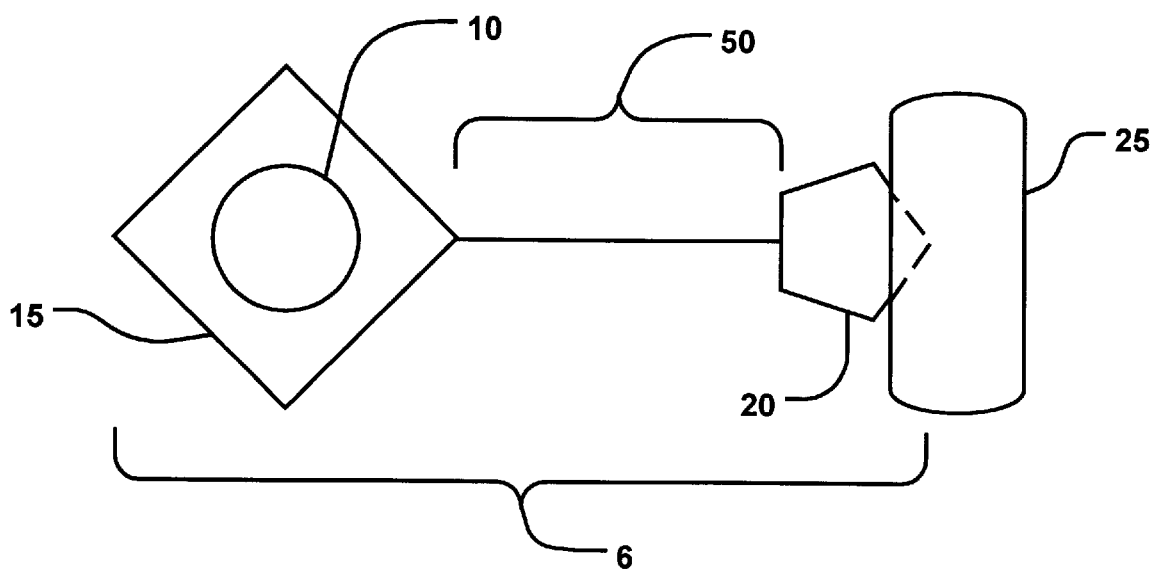
FIG. 9B is the eighth sensor embodiment, seen in FIG. 9A, bound to a target species.

Clearly, the embodiments structures depicted in FIGS. 1–8 for the basic subject biosensor may contain additional useful components/structures. As seen in FIGS. 9A and 9B, one, or more. "tether" or "linker" or "spacer" regions 50 may be included in the biosensor 6. Specifically, FIG. 9A shows a biosensor comprising a first binding region 15 for the active-nucleus, a bound active-nucleus 10, a second binding region 20 for the target, and a tether 50. The tether 50 serves to separate the first 15 and second 20 binding regions and may serve as a site where chemical modification can occur. FIG. 9B illustrates the binding of the second binding group 20 with a target 25. The chemical nature of the tether may be varied and includes polymethylenes, homo and heteropolymers, polyethers, amides, various functional group combinations, amino acids, carbohydrates, and the like. If desired, a plurality of tethered second binding groups may be bound to a first binding region, with each tether and/or second binding group the same or different.

The tether may be derivatized to include a solubilizing region or other desired chemical feature such as additional binding sites and the like. The solubilizing region aids in solubilizing the biosensor in either a hydrophilic or hydrophobic environment. It is noted that a solubilizing region may also be included, either in addition to or separately, in the first and/or second binding regions. A water solubilizing region may include generally hydrophilic groups such as peptides, carbohydrates, alcohols, amines, and the like (for a specific example see FIGS. 11 and 12).

Figure 10:
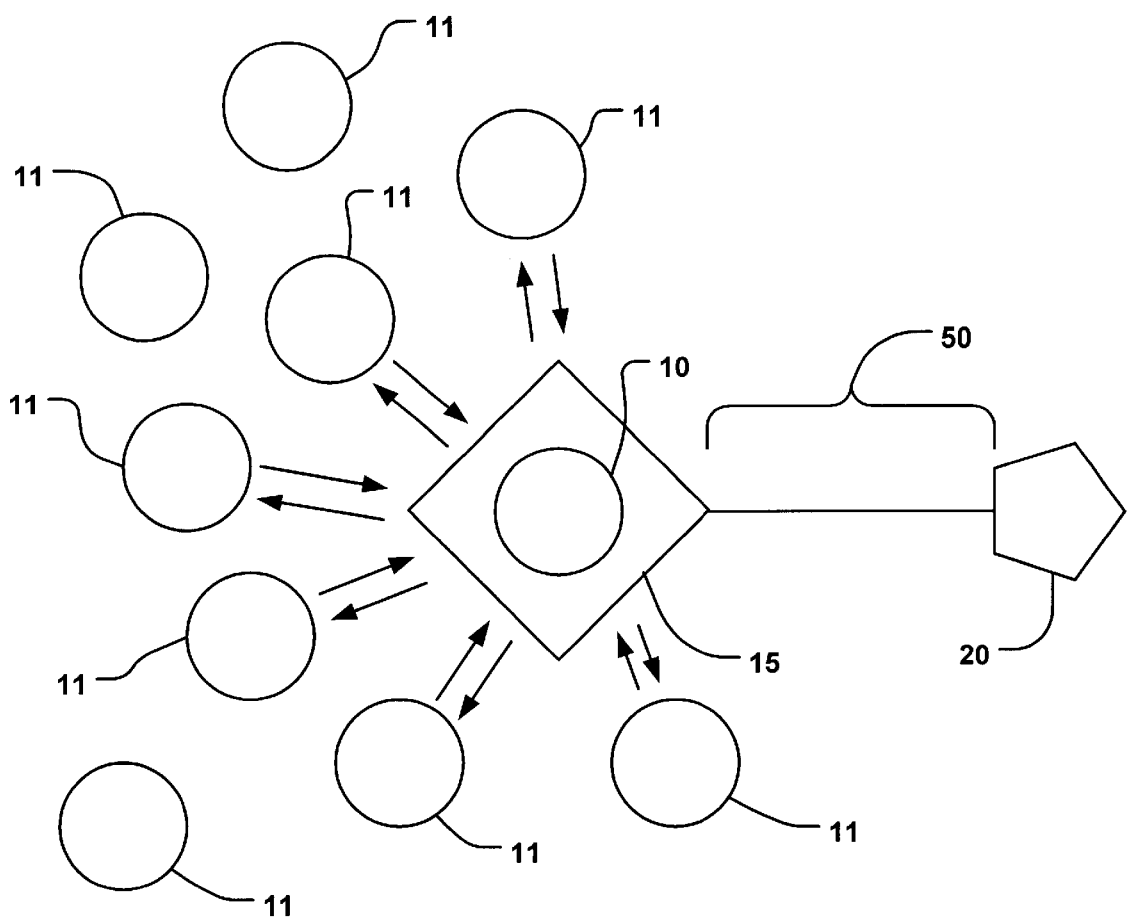
FIG. 10 is the eighth sensor embodiment, seen in FIG. 9A, illustrating an active-nuclei exchange process that enhances the generated detection signal.

FIG. 10 illustrates a subject biosensor in which the signal is enhanced by a rapid chemical exchange of the active-nuclei. Free active-nuclei 11 rapidly exchange with the active-nucleus 10 bound in the first binding region 15 to produce an overall increase in sensitivity by enhancing the signal.-

More specifically, a functionalized active-nucleus biosensor is disclosed that capitalizes on the enhanced signal to noise, spectral simplicity, and chemical shift sensitivity of a hyperpolarized xenon to detect specific biomolecules at the level of tens of nanomoles. Optical pumping (6) has enhanced the use of xenon as a sensitive probe of its molecular environment (7,8). Laser-polarized xenon has been utilized as a diagnostic agent for medical magnetic resonance imaging (MRI) (9) and spectroscopy (10), and as a probe for the investigation of surfaces and cavities in porous materials and biological systems. As indicated for an active-nucleus, xenon provides information both through direct observation of its NMR spectrum (11-17) and by the transfer of its enhanced polarization to surrounding spins (18,19). In a protein solution, weak xenon-protein interactions render the chemical shift of xenon dependent on the accessible protein surface, and even allow the monitoring of the protein conformation (20). In order to utilize xenon as a specific sensor of target molecules the xenon was functionalized for the purpose of reporting specific interactions with the molecular target.

Specifically, a laser polarized xenon was "functionalized" by a biotin-modified supramolecular cage to detect biotin-avidin binding, thus, the specific target is avidin. Although, as previously indicated, the first binding region that holds the active-nucleus may be one of many possible structures, one suitable first binding region or cage is a member of the cryptophane family. Cryptophane has the following structure:

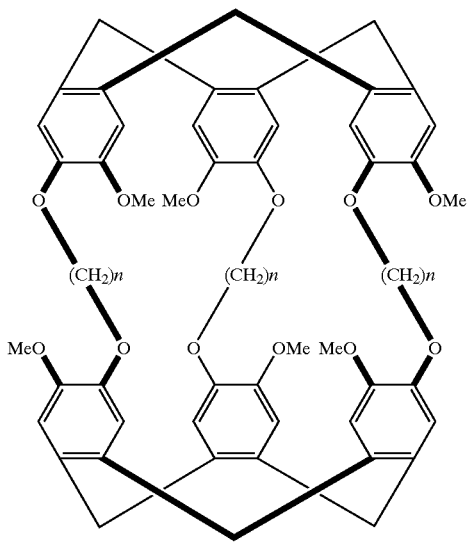

Formula I

Wherein n=2 for cryptophane-A or n=3 for cryptophane-E.

Figure 11:
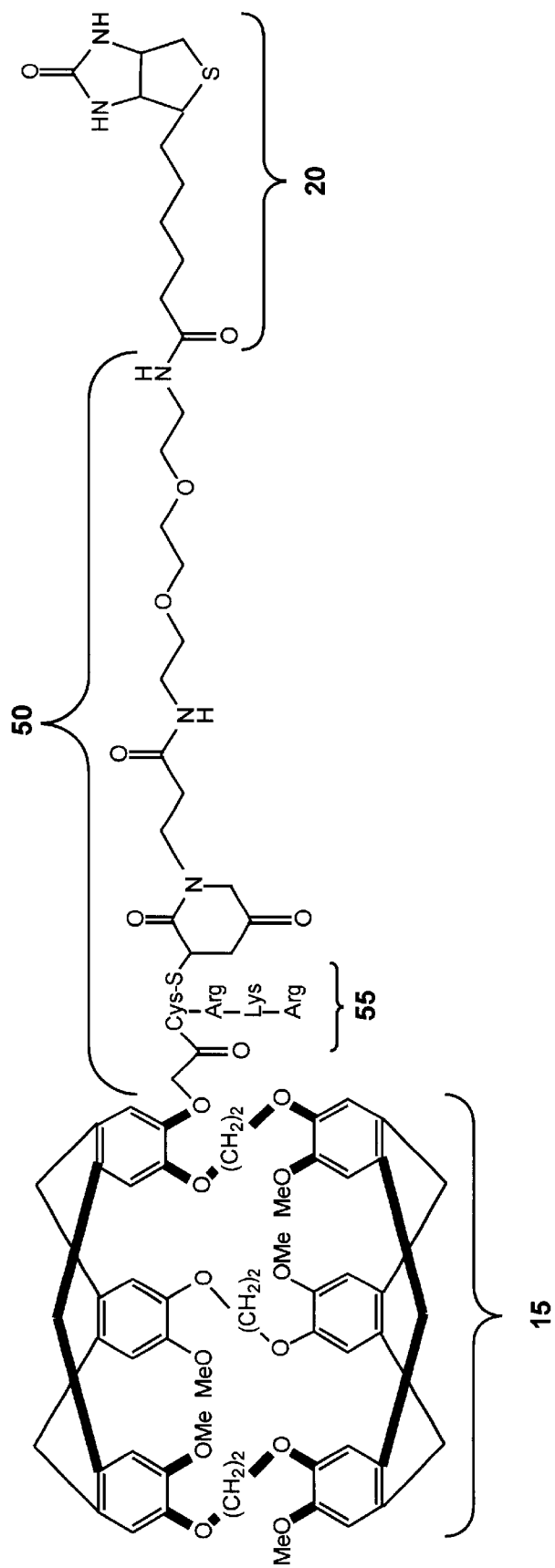
FIG. 11 is a specific chemical structure of the subject sensor, without an active-nucleus, showing a first binding region (cryptophane-A) for holding the active-nucleus, a second binding region that associates with the target, a tether region that connects the first and second binding regions, and a solubilizing polypeptide attached to the tether.

FIG. 11 (showing Formula II) depicts a specific targeting carrier in which the first binding region cryptophane-A 15 is covalently attached to a tether 50, having a solubilizing region 55, and biotin as the second binding region 20 (see the Example #1 below for synthesis details). The solubilizing region comprises a short peptide chain (Cys-Arg-Lys-Arg) having positively charged groups at physiological pH values.

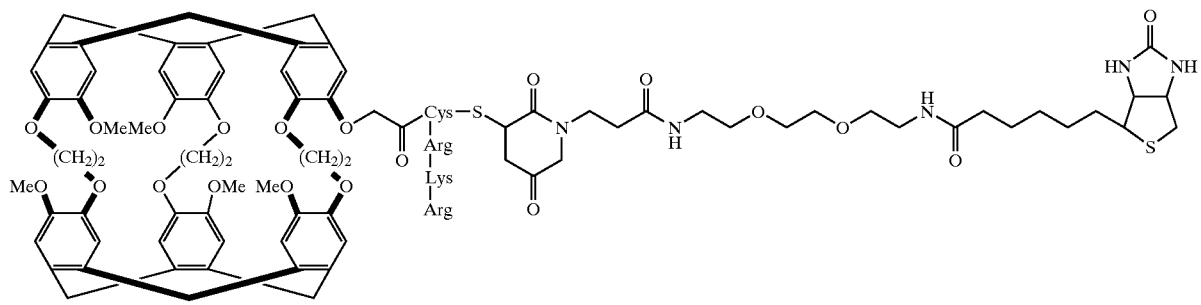

Formula II

Figure 12:
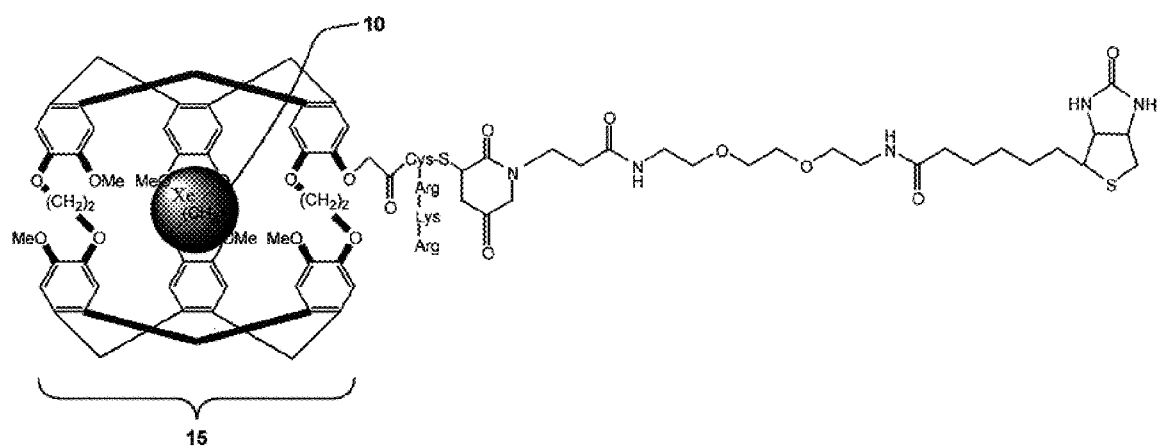
FIG. 12 is the specific chemical structure shown in FIG. 11 with the active-nucleus xenon included within the cage-like, cryptophane-A, first binding region.

FIG. 12 (showing Formula III) shows the functionalized active-nucleus biosensor when the xenon 10 is bound within the first binding region cryptophane-A 15 cage.

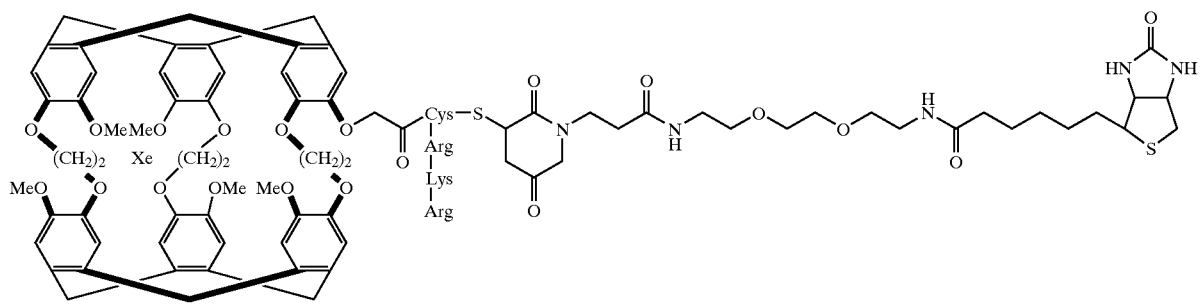

Formula III

EXPERIMENTAL EXAMPLE #1

Functionalized Xenon as a Biosensor

By way of example and not by way of limitation, one embodiment of the subject invention comprises a functionalized system that exhibits molecular target recognition. FIGS. 11 (without xenon) and 12 (with xenon) show a biosensor molecule designed to bind both xenon and protein. Analogous to the general schematic diagrams seen in FIGS. 9A and 9B, the specifically synthesized subject biosensor molecule consists of three parts: the cage 15, which contains the xenon 10; the ligand 20, which directs the functionalized xenon 10 to a specific protein; and the tether 50, which links the ligand 20 and the cage 15. In this molecule, it is expected that the binding of the ligand 20 to the target protein (as in analogous FIG. 9B) will be reflected in a change of the xenon NMR spectrum.

The biotin (ligand second binding region 20) and avidin (target species) couple was chosen because of its high association constant ($\sim10^{15}$ M$^{-1}$) (21) and the extensive literature characterizing binding properties of modified avidin or biotin (22). The cage 15 chosen for this embodiment was a cryptophane-A molecule (23) with a polar peptide chain (solubilizing region 55) attached in order to make the cryptophane-A water-soluble.

The cryptophane-A-based biosensor molecule was synthesized by a modified template directed procedure (23). Starting from 3,4-dihydroxybenxaldehyde and using allyl bromide to reversibly protect the meta-hydroxyl group (24), one of the 6 methoxyl groups in cryptophane-A was regioselectively replaced with a free hydroxyl group. Upon reacting with methyl bromoacetate followed by hydrolysis (25), the hydroxyl group in the modified cryptophane-A was converted to a carboxylic acid, which was subsequently coupled (using HOBt/HBTU/DIEA activation method) to the amino-terminus of a protected short peptide CysArgLysArg on rink amide resin. The resulting cryptophane-A-peptide conjugate was deprotected and cleaved off the resin using "Reagent K" (26), followed by purification with RP-HPLC (MicrosorbTM 80210C5, RP-C18 column, flow 4.5 ml/min, buffer A: 0.1% TFA in H$_2$O, buffer B: 0.1% TFA in CH$_3$CN, linear gradient from 40% to 80% buffer B in 30 min). The purified conjugate was reacted with EZ-link TMPEO-Maleimide activated biotin (Pierce) to give the desired functionalized water-soluble cryptophane-A, which was further purified by RP-HPLC (same conditions). The last two peptide conjugated-products were is verified by matrix-assisted laser desorption/ionization (MALDI)-time of flight-(TOF) mass spectrometry. All other intermediates were confirmed by $^1$H NMR and MALDI-Fourier Transform mass spectrometry (FTMS).

Cryptophane-A has been shown to bind xenon with a binding constant K$\approx10^3$ M$^{-1}$ in organic solvents (15) but the affinity is likely to increase in aqueous solution because of the hydrophobic nature of xenon. The characteristic chemical shift for xenon inside a cryptophane-A molecule is very unusual for xenon dissolved in solution, approximately 130 ppm upfield from that of xenon in water. The only background xenon signal in the sample arises from xenon free in solvent, so the signal from the functionalized xenon is easily distinguishable. In the design of a xenon biosensor, a separate peak corresponding to xenon encapsulated by the cage is necessary, requiring both strong binding and a large difference between the xenon chemical shifts in the cage and solvent environments. The spin-lattice relaxation time for the functionalized xenon described herein was measured to be greater than 40 s, sufficient time for the required transfer, mixing, and detection of the polarized xenon.

The biosensor solution was prepared by dissolving ~0.5 mg of the cryptophane derivative (M.W.=2008 g mol$^{-1}$) in 700 µL of D$_2$O, yielding a concentration of ~300 µM. This concentration was consistent with absorbance measurements at 284 nm ($\epsilon_{284}$=36,000 M$^{-1}$ cm$^{-1}$, determined for unmodified cryptophane-A by successive dilutions of a solution of known concentration). Approximately 80 nmol of affinity purified egg white avidin (Sigma) was used without further purification. Only half of the sample was located inside the detection region, so spectra actually reflect detection of ~40 nmol avidin monomer. Natural abundance xenon (Isotec) was polarized and introduced to the sample using previously described methods (16), showing ~5% polarization for the spectra shown in FIGS. 13 and 14. All NMR spectra displayed were obtained in single acquisition experiments at a nominal $^{129}$Xe frequency of 82.981 MHz.

Figure 13:
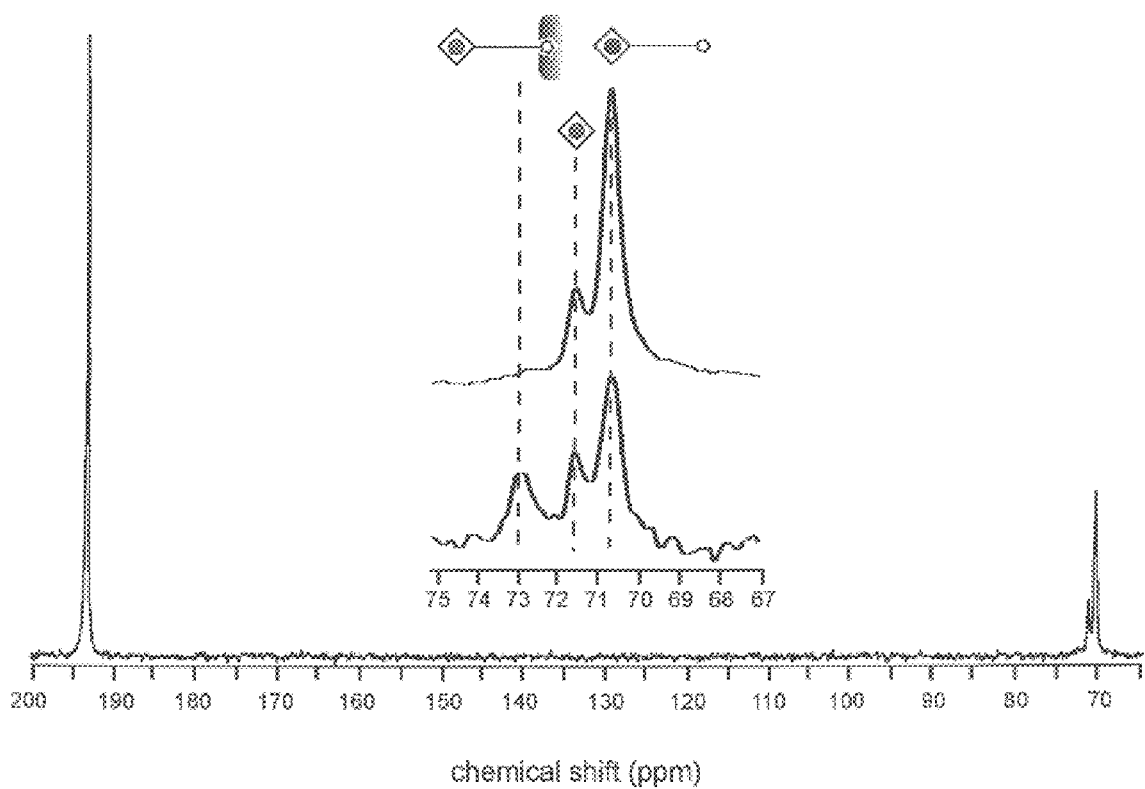
FIG. 13 shows $^{129}$Xenon NMR spectra that monitors the binding of a biotin-functionalized xenon biosensor to avidin.

FIG. 13 shows the full $^{129}$Xe NMR spectrum of the functionalized xenon in the absence of protein (the trace running near the bottom axis and having a far left peak and far right peaks). The far left peak at 193 ppm corresponds to xenon free in water while the far right peaks around 70 ppm are associated with xenon-bound cryptophane-A. The far right peaks are shown expanded in the center of FIG. 13, where the more intense, upfield peak (~70.7 ppm) corresponds to functionalized xenon and has a linewidth of 0.15 ppm (shown by the generalized schematic model, as seen in FIG. 9A). A smaller, middle peak (~71.5 ppm) approximately 1 ppm downfield of the functionalized xenon peak is attributed to xenon bound to a bare cage, without linker and ligand. As the unfunctionalized caged xenon does not interact specifically with the protein, it serves as a useful reference for the chemical shift and signal intensity of the functionalized xenon in the binding event.

Upon addition of ~80 nmol of avidin monomer, a third peak (~73 ppm) appears approximately 2.3 ppm downfield of the functionalized xenon peak, attributable to functionalized xenon bound to the protein. Correspondingly, the peak assigned to free functionalized xenon decreases in intensity relative to the reference peak while its position remains unchanged. The peak (~73 ppm) observed upon the addition of avidin is an unambiguous identifier of biotin-avidin binding, and hence the presence of avidin in solution.

The mechanism of the chemical shift change upon binding may result from actual contact between the cryptophane cage and the protein, leading to cage deformation and distortion of the xenon electron cloud. Changes in the rotational and vibrational motions of the cryptophane cage caused by binding to the protein could also affect the xenon chemical shift. Indeed, the sensitivity of xenon to perturbations of the first binding region cage is so great that deuteration of one methyl group results in a readily discernible change in the bound xenon chemical shift (17).

Figure 14:
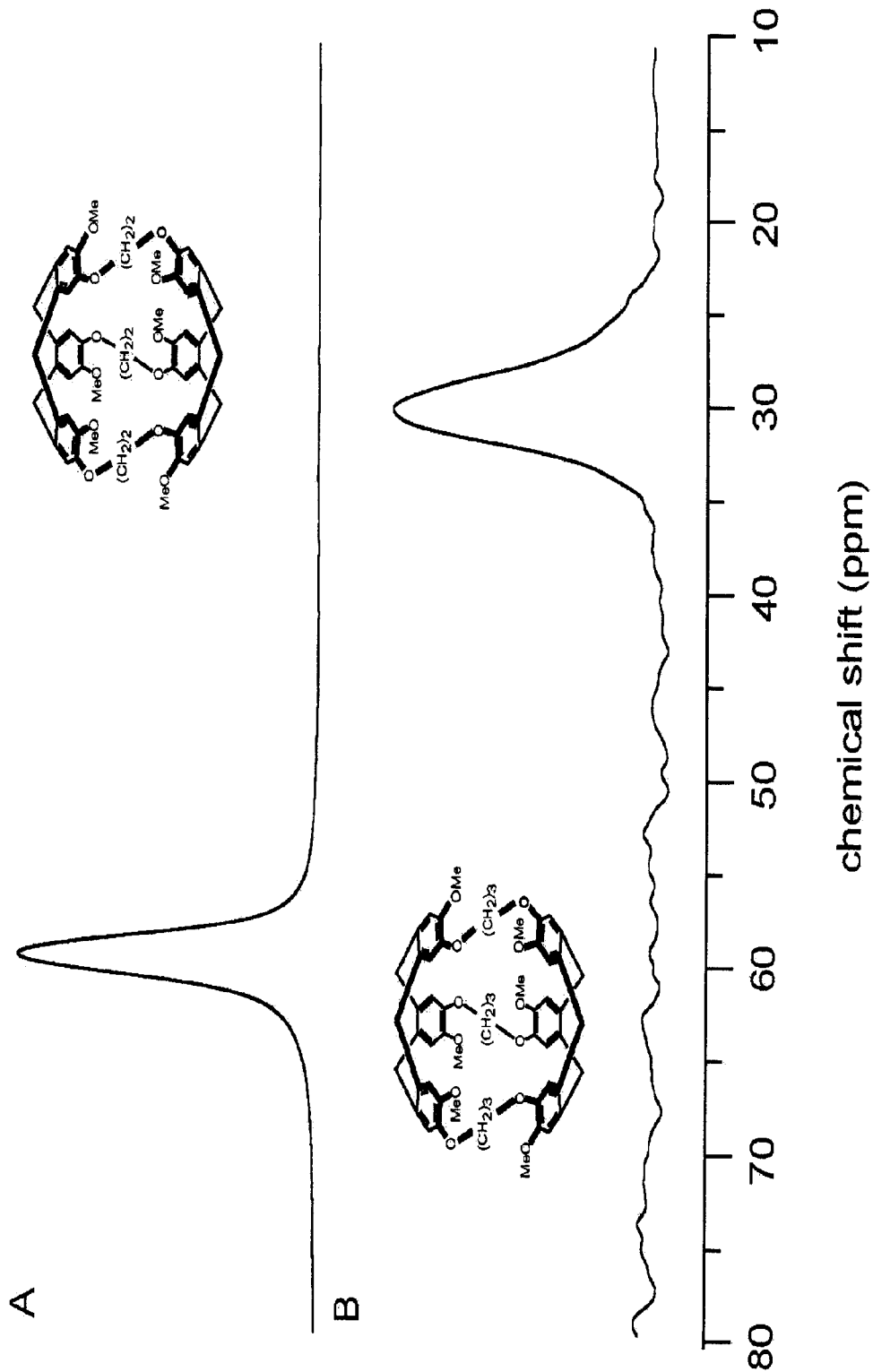
FIG. 14 shows the effect of cage structure (cryptophane-A in the top "A" view and cryptophane-E in the bottom "B" view) on the bound xenon chemical shift.

The subject methodology described herein offers the capability of multiplexing by attaching different second binding regions ligands to different first binding region cages, forming xenon sensors associated with distinct, resolved chemical shifts. As an example of this feature of the subject invention, FIG. 14 shows the changes in bound xenon chemical shift caused by using two different first binding region cages. The top spectrum A is that of xenon bound to cryptophane-A (n=2 in Formula 1 above) in a tetrachloroethane solution and the lower spectrum B is that of xenon bound to cryptophane-E (n=3 in Formula 1 above), similar to cryptophane-A, but with an additional methylene group added to each of the bridges between the caps. The resulting bound xenon chemical shift is ~30 ppm upfield from that of xenon bound to cryptophane-A. The linewidths for cryptophanes A and E are broadened by the exchange of xenon between the cage and tetrachloroethane, the organic solvent used.

Figure 15:
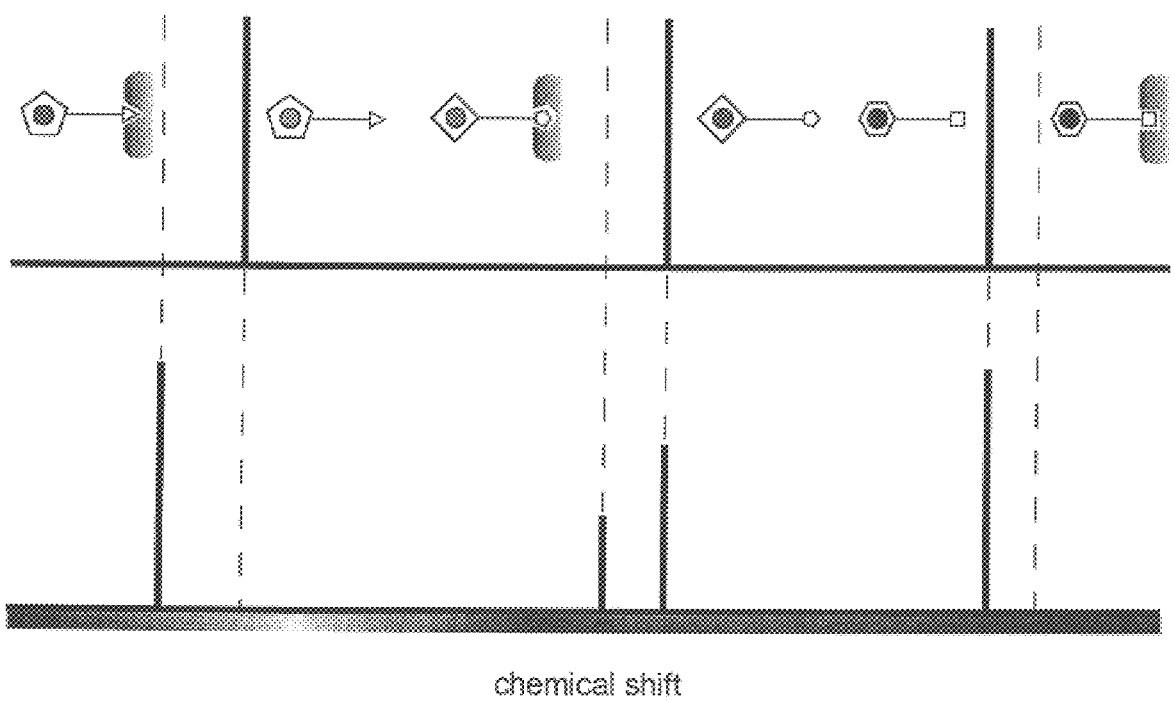
FIG. 15 is a schematic diagram showing multiplexing with functionalized xenon biosensors in which the top spectrum shows the three distinct functionalized xenon peaks, corresponding to different first binding region cages tethered to three second binding region ligands. The bottom spectrum shows the effect of adding the functionalized xenon biosensor to an unknown sample solution having targets.

The diagram in FIG. 15 indicates schematically a multiplexing system (multiple functionalized xenon biosensors) for protein assay or screening procedures. The binding event assay/screening procedures would be distributed over a large chemical shift range by attaching each second binding region ligand to a different first binding region cage. In the absence of the targeted proteins, the spectrum, depicted in FIG. 15, would consist of three resolved xenon resonances because of the effect on the xenon chemical shift caused by cage modifications. Upon binding each of the targeted proteins, the xenon peaks should shift "independently," signaling each binding event and reporting the existence of and amount of protein present. As long as the differences in shift between xenon in the different cages exceed the shift change upon binding, it should be possible to monitor and assign multiple binding events. In FIG. 15, the top spectrum shows the three distinct functionalized xenon peaks, corresponding to different cages linked to three ligands. The bottom spectrum shows the effect of adding the functionalized xenon to an unknown solution. Upon addition to the unknown solution, the leftmost peak shifts entirely, representing the case in which all functionalized xenon is bound to its corresponding protein. The central peak decreases in intensity and a peak corresponding to the protein-bound functionalized xenon appears. The rightmost peak remains unaffected, indicating the absence of the corresponding protein target.

Thus, enabling experimental data for the subject functionalized active-nucleus biosensor has been disclosed that exploits the chemical shift of functionalized xenon upon binding to a target species/substrate/molecule/analyte. The approach has several critical advantages over aspects of current biosensors, in that multiplexing assays and both heterogeneous and homogenous assays are possible. Furthermore, this methodology can be performed in biological materials in vitro or in vivo by combining the spatial encoding capabilities of MRI with the biosensing NMR capabilities of the functionalized xenon sensor. As indicated above, potential targets include, are not limited to, metabolites, proteins, toxins, nucleic acids, and protein plaques. It must be stated that, given the basic information presented herein, refinements of the subject functionalized detector molecules/sensors and the NMR procedures disclosed herein should further enhance the presented sensitivity by orders of magnitude, relative to the experimental example described herein and are within the realm of this disclosure.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

REFERENCES

All of the following references are herein incorporated by reference. In particular, reference 16 (S. M. Rubin, M. M. Spence, B. M. Goodson, D. E. Wemmer, A. Pines, *Proceedings of the National Academy of Sciences of the United States of America* 97, 9472–9475 (2000)) was in the original subject Provisional Application and is specifically incorporated herein by reference, as are all of the Provisional Application file documents.

1. M. Malmqvist, *Nature* 361, 186–187 (1993).
2. W. J. Checovich, R. E. Bolger, T. Burke, *Nature* 375, 254–256 (1995).
3. A. Miyawaki et al., *Nature* 388, 882–887 (1997).
4. S. B. Shuker, P. J. Hajduk, R. P. Meadows, S. W. Fesik, *Science* 274, 1531–1534 (1996).
5. A. Y. Louie et al., *Nature Biotechnology* 18, 321–325 (2000).
6. T. G. Walker, W. Happer, *Reviews of Modern Physics* 69, 629–642 (1997).
7. C. I. Ratcliffe, *Annual reports on NMR spectroscopy* 36, 124–208 (1998).
8. Y. Q. Song, B. M. Goodson, A. Pines, *Spectroscopy* 14, 26–33 (1999).
9. M. S. Albert et al., *Nature* 370, 199–201 (1994).
10. J. Wolber, A. Cherubini, M. O. Leach, A. Bifone, *Magnetic Resonance in Medicine* 43, 491–496 (2000).
11. C. R. Bowers et al., *Journal of the American Chemical Society* 121, 9370–9377 (1999).
12. R. F. Tilton, I. D. Kuntz, *Biochemistry* 21, 6850–6857 (1982).
13. M. A. Springuel-Huet, J. L. Bonardet, A. Gedeon, J. Fraissard, *Magnetic Resonance in Chemistry* 37, S1–S13 (1999).
14. M. Luhmer et al., *Journal of the American Chemical Society* 121, 3502–3512 (1999).
15. K. Bartik, M. Luhmer, J. P. Dutasta, A. Collet, J. Reisse, *Journal of the American Chemical Society* 120, 784–791 (1998).
16. S. M. Rubin, M. M. Spence, B. M. Goodson, D. E. Wemmer, A. Pines, *Proceedings of the National Academy of Sciences of the United States of America* 97, 9472–9475 (2000).
17. T. Brotin, A. Lesage, L. Emsley, A. Collet, *Journal of the American Chemical Society* 122, 1171–1174 (2000).
18. G. Navon et al., *Science* 271, 1848–1851 (1996).
19. C. Landon, P. Berthault, F. Vovelle, H. Desvaux, *Protein Science* 10, 762–770 (2001).
20. S. M. Rubin et al., submitted to *Journal of the American Chemical Society*, (2001).
21. P. C. Weber, D. H. Ohlendorf, J. J. Wendoloski, F. R. Salemme, *Science* 243, 85–88 (1989).
22. M. Wilchek, E. A. Bayer, *Methods in Enzymology* 184, 14–45 (1990).
23. A. Collet, *Tetrahedron* 43, 5725–5759 (1987).
24. S. N. Kilenyi, J. M. Mahaux, E. Vandurme, *Journal of Organic Chemistry* 56, 2591–2594 (1991).
25. J. Canceill, A. Collet, G. Gottarelli, P. Palmieri, *Journal of the American Chemical Society* 109, 6454–6464 (1987).
26. D. S. King, C. G. Fields, G. B. Fields, *International Journal of Peptide and Protein Research* 36, 255–266 (1990).

What is claimed is:

1. A functionalized active-nucleus complex that selectively associates with a biological target species, wherein the functionalized active-nucleus complex comprises:
   a) an active-nucleus and
   b) a cryptophane family member targeting carrier comprising:
      i) a first binding region having at least a minimal transient binding of said active-nucleus to form the functionalized active-nucleus complex that produces a detectable signal when the functionalized active-nucleus complex associates with the target species and ii) a second binding region, non-coextensive with said first binding region, that selectively associates with the target species.

2. A functionalized active-nucleus complex according to claim 1, wherein the functionalized active-nucleus complex is selected from a group consisting of a nuclear magnetic resonance reporter species and a magnetic resonance imaging contrast agent.

3. A functionalized active-nucleus complex according to claim 1, wherein said active-nucleus is selected from a group consisting of hyperpolarized xenon, sulfur hexafluoride, $^{19}F$, and hyperpolarized helium.

4. A functionalized active-nucleus complex according to claim 1, wherein:

a) said active-nucleus comprises hyperpolarized xenon and b) said first binding region comprises a cryptophane family member.

5. A functionalized active-nucleus complex according to claim 4, further comprising a solubilizing region associated with said targeting carrier.

6. A functionalized active-nucleus complex according to claim 5, wherein said solubilizing region comprises a moiety that enhances the solubility of the functionalized active-nucleus complex in a desired environment.

7. A functionalized active-nucleus complex that selectively associates with a biological target species, wherein the functionalized active-nucleus complex comprises:

a) an active-nucleus, wherein said active-nucleus comprises hyperpolarized xenon:

b) a targeting carrier comprising:

i) a first binding region having at least a minimal transient binding of said active-nucleus to form the functionalized active-nucleus complex that produces a detectable signal when the functionalized active-nucleus complex associates with the target species, wherein said first binding region comprises a cryptophane ii) a second binding region that selectively associates with the target species: and c) a solubilizing region associated with said targeting carrier wherein said solubilizing region comprises at least one amino acid.

8. A functionalized active-nucleus complex according to claim 4, further comprising a tether connecting said first and second binding regions.

9. A functionalized active-nucleus complex according to claim 8, further comprising a solubilizing region comprising a moiety bound to said tether.

* * * * *